United States Patent [19]

Garabedian

[11] Plant 5,137

[45] Nov. 15, 1983

[54] PLUM TREE

[76] Inventor: John M. Garabedian, 3104 E. Huntington Blvd., Fresno, Calif. 93702

[21] Appl. No.: 294,038

[22] Filed: Aug. 18, 1981

[51] Int. Cl.[3] ..... A01H 5/00
[52] U.S. Cl. ..... Plt./38
[58] Field of Search ..... Plt./38

*Primary Examiner*—James R. Feyrer
*Attorney, Agent, or Firm*—Vergil L. Gerard

[57] ABSTRACT

Disclosed is a new and distinct variety of plum tree characterized in its comparison with the Nubiana plum which it most nearly resembles but is an improvement thereon in ripening much earlier, between May 14 and May 21, is slightly more oblate and compressed in shape, has a more attractive dark maroon to almost black skin color when ripe, and a richer, vinuous flavor. The instant variety also ripens more than one week earlier than the Red Beaut (patented) which is the conventional earliest plum variety.

2 Drawing Figures

1

The present discovery relates to a plum tree and more particularly to a new and distinct variety thereof broadly characterized by bearing fruit which is oblate to slightly globose in form, almost solid black in color when shipping ripe and dark maroon at first picking, and which ripens more than one week earlier than the Red Beaut patented variety.

Although the instant variety most nearly resembles the Nubiana variety, it is distinguished therefrom and is an improvement thereon in that its fruit is slightly more oblate and compressed in shape and has a more attractive dark maroon color when ripe, a distinct and alluring aroma, and a rich, vinuous flavor, and the fruit ripens much earlier than the Nubiana and more than a week earlier than the conventional earliest plum variety, the Red Beaut. The instant variety is also distinguishable from the Nubiana by the characteristics of its fruit stone which is unusually non-uniform in size and appearance, has a highly irregular periphery, and irregularly furrowed surface. Also, it has been found that virtually none of the kernels from the fruit stones of the instant variety will germinate.

The present variety originated on a farm owned by me in Fresno County, Calif., appearing as a sport on a Nubiana plum tree used as a pollinator in an orchard of Red Beaut plum trees. The new variety was asexually reproduced by budding over budwood from said sport onto Red Beaut trees. The new variety thus asexually reproduced fully maintained its original characteristics.

The accompanying photographs show the following characteristics: twigs and leaves of the subject plum tree, fruit at maturity showing the dark maroon skin coloration, fruit at first picking when the skins show more reddish coloration, a characteristic fruit cut on the suture line showing flesh and pit coloration, and stones. All major color plate identifications are by reference to Maerz and Paul's Dictionary of Color, 1st Ed.

Referring now more specifically to the pomological characteristics of this new and distinct variety of plum tree, the following has been observed under the ecological conditions prevailing at Fresno, Fresno County, Calif. and is an outline description thereof.

2

TREE

General: Small size, vigorous, hardy; upright with open, vase shaped branches; productive and regular bearer, with adequate pollination.

Trunk: Medium size and medium shaggy; dark gray color with some lighter patterns.

Branches: Medium size, medium shaggy; glossy on dorsal side, dull green on ventricle side; dorsal side slight brown over green. Two year wood, dorsal side dark gray, strictions lighter, raised; ventricle side dark brownish gray. Numerous lenticles, small on small wood, large ($\frac{1}{8}''$–$\frac{1}{4}''$) on older wood; horizontal, numerous on trunk and lighter in color.

Leaves: 99 mm average length, 42 mm average width, large to medium size; elliptical form, thin, dark green, smooth and glabrous. Color 23 L-10 Polo Green on dorsal side, 29 A-7 Celadine Green on ventral side. Acuminate apex, mostly acute base, pinnately net veined, crenate margin. Petiole short, average 8.7 mm; thick, average 1.9 mm; slight brownish red over green on dorsal, 28 J-4 Rainette Green on ventral side. Glands, average 3.6, small, globose, opposite; green on peitiole; one $\frac{1}{4}''$ stipule from 10 leaves. Small, pointed leaf bud.

FLOWERS

Buds: Hardy, small, short, plump, free and glabrous.

Flowers: First bloom Feb. 24, 1980, full bloom Mar. 8, 1980; white; approximately 1 week to 10 days earlier than Red Beaut.

FRUIT

Shipping: Ripe, few green, few eating ripe when described; first picking May 14, 1980, last picking May 21, 1980. In same location, Red Beauts being picked May 27, 1980.

Size: Mostly medium, many large; $1\frac{7}{8}''$ axial diameter, 1 14/16" transverse in suture plane.

Form: Uniform, symmetrical, oblate toward suture, mostly round. Very slightly oblate transverse through diameter. Suture distinct, extends from base to beyond but discontinues at apex, has marked depression at pistil point.

Ventral surface: Slightly rounded, slightly lipped toward base on both sides, equal lips.

Cavity: Flaring, rounded and elongated in suture plane with suture showing on one side; 10.5 mm average depth, 17 mm average breadth.
Base: Truncated, short, depressed, apical apex.
Stem: 11 mm average length, $1\frac{7}{8}$ mm average width.

SKIN

Thin, tender, slightly bitter, tenacious to flesh but free on ripe fruit, slight tendency to crack near apex; mostly solid black, many black below base to apex with shoulders 7 L-7 Maroon, some immature fruit greenish with red over-color at shoulder; wanting in down, with a faint to moderate bloom.

FLESH

Color: Light cream to yellow throughout (10 G-3 Cornsilk).
Pit cavity: Light cream to yellow, (10 G-3 Cornsilk).
Amygdalin: Wanting; moderate juice.
Texture: Firm to medium, fine, crisp, melting.
Fibres: Few fine, tender.
Ripens: Evenly, earliest at apex along cheeks.
Flavor: Slightly acid to delicate, vinuous.
Aroma: Distinct to very slight.
Eating quality: Very good to best.

STONE

Free on eating ripe fruit to semi-free on shipping ripe fruit over both dorsal and ventral edges and over upper half of sides; short fibers, retains short fiber-like threads along ridges at upper half of fruit.
Size: Large to medium, mostly medium; 11 mm average breadth, 16 mm average thickness.
Form: Obovoid, full cuneate toward base; base straight, hilum broad. Most stones have protruding wing on dorsal ridge at lower apex end of stone.
Apex: Flattened with short, sharp point at apex end.

Surface: Irregularly furrowed throughout; ridged throughout; pitted throughout, more heavily near apex.
Ridges: Jagged toward base and apex.
Pits: Circular and irregular.
Ventral edge: Thick, slight wing toward base, with grooves variable.
Dorsal edge: Full, narrow groove throughout with wing at apex end.
Ridges: On either side, interrupted, few continuous.
Stone: 10 G-5 Maize, 1 mm to 3 mm thickness of pit wall, no tendency to split.
Kernel: Ovate, slightly bitter taste, 33% viable. 7 mm in width, 7 mm length, 4 mm thick. 11 K-9 Dubloon Roman Ochre color, scant amygdalin.
Germination: Nearly impossible to germinate.

USE

For market: Good keeping quality, good resistance to insects, good shipping quality.

Having thus described a new plum tree, what is claimed is:

1. A new and distinct variety of plum tree substantially as illustrated and described and being characterized by its early maturity, approximately one week to ten days earlier than the Red Beaut variety; by fruit which is slightly more oblate and compressed in shape than fruit of the Nubiana variety, has a more attractive dark maroon color when ripe than the Nubiana, a distinctive and alluring aroma, and a richer, more vinuous flavor than fruit of the Nubiana, and has a fruit stone which is characterized by its non-uniformity in size and shape, its irregular periphery, and its irregularly furrowed surface.

* * * * *

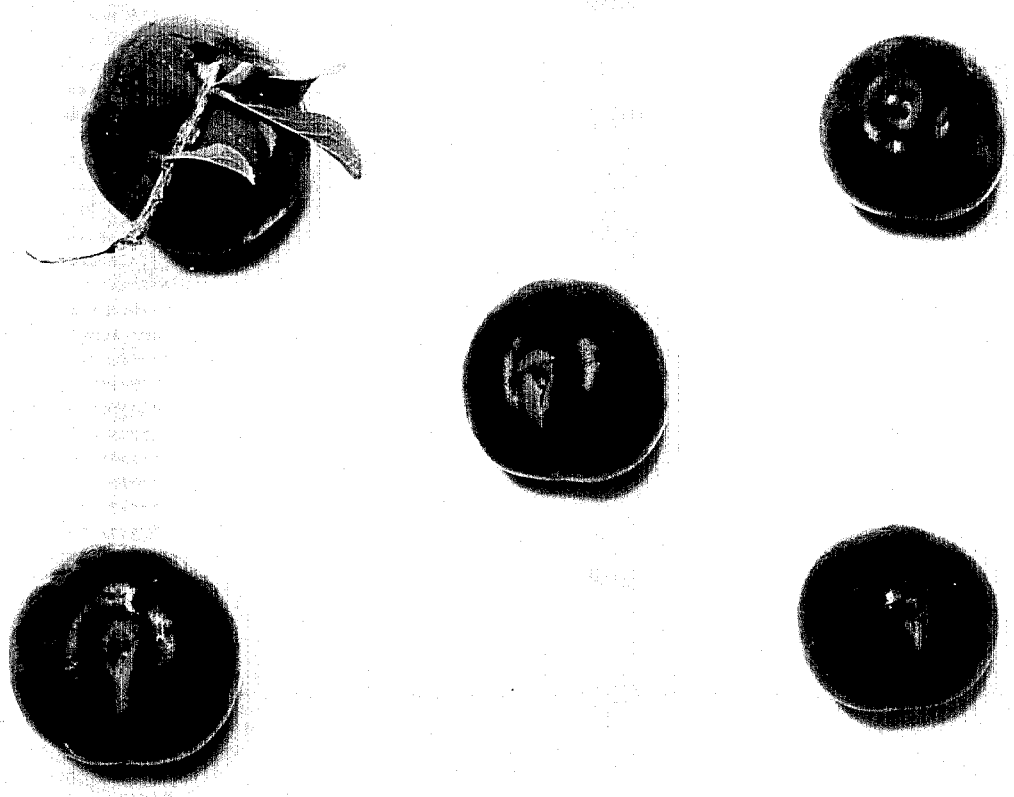

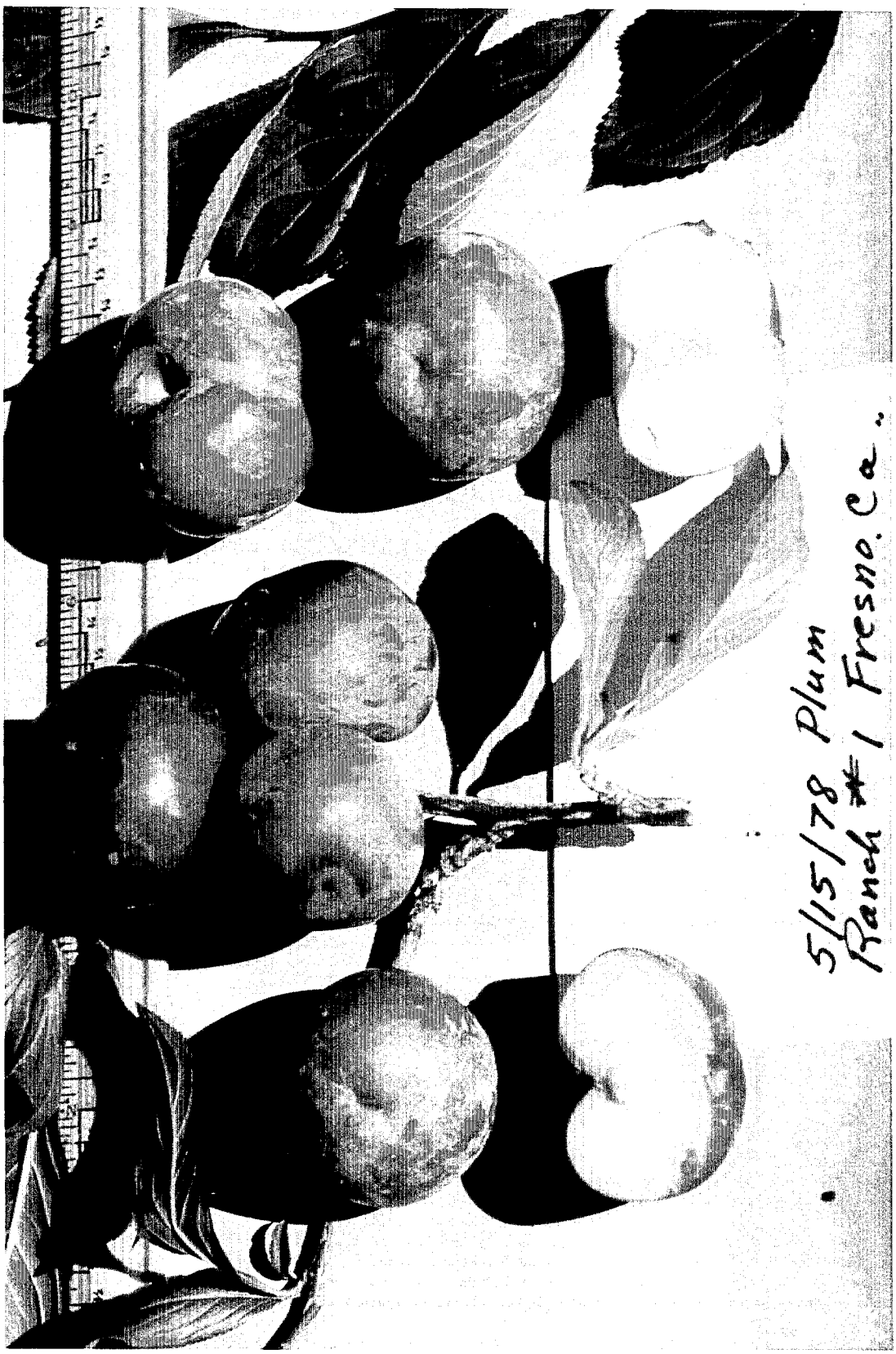
5/15/78 Plum
Ranch #1 Fresno Ca.